(12) United States Patent
Onji et al.

(10) Patent No.: US 11,022,556 B2
(45) Date of Patent: Jun. 1, 2021

(54) TETRAZOLIUM COMPOUND FOR DETECTING MICROORGANISMS, REAGENT FOR DETECTING MICROORGANISMS AND METHOD FOR DETECTING MICROORGANISMS

(75) Inventors: Yuichi Onji, Yokohama (JP); Masashi Ushiyama, Yokohama (JP)

(73) Assignee: JNC CORPORATION, Tokyo (JP)

( * ) Notice: Subject to any disclaimer, the term of this patent is extended or adjusted under 35 U.S.C. 154(b) by 111 days.

(21) Appl. No.: 13/641,224

(22) PCT Filed: Mar. 16, 2011

(86) PCT No.: PCT/JP2011/056175
§ 371 (c)(1),
(2), (4) Date: Oct. 15, 2012

(87) PCT Pub. No.: WO2011/132480
PCT Pub. Date: Oct. 27, 2011

(65) Prior Publication Data
US 2013/0210065 A1 Aug. 15, 2013

(30) Foreign Application Priority Data

Apr. 19, 2010 (JP) .............................. JP2010-096510

(51) Int. Cl.
*G01N 21/78* (2006.01)
*C07D 257/04* (2006.01)
*C12Q 1/04* (2006.01)

(52) U.S. Cl.
CPC ........... *G01N 21/78* (2013.01); *C07D 257/04* (2013.01); *C12Q 1/04* (2013.01)

(58) Field of Classification Search
CPC ......... G01N 21/78; C07D 257/04; C12Q 1/04
See application file for complete search history.

(56) References Cited

U.S. PATENT DOCUMENTS

| | | | |
|---|---|---|---|
| 3,749,768 A | 7/1973 | Kalopissis et al. | |
| 4,284,704 A | 8/1981 | Fleming et al. | |
| 4,565,783 A | 1/1986 | Hansen et al. | |
| 5,089,413 A | 2/1992 | Nelson et al. | |
| 5,360,595 A * | 11/1994 | Bell ..................... | G01N 33/521 422/420 |
| 6,265,203 B1 | 7/2001 | Ushiyama | |
| 7,312,072 B2 | 12/2007 | Ushiyama et al. | |
| 2002/0192742 A1 | 12/2002 | Ushiyama et al. | |
| 2005/0084948 A1 | 4/2005 | Ushiyama et al. | |
| 2006/0008867 A1* | 1/2006 | Ushiyama ............. | C12N 1/20 435/34 |
| 2007/0238139 A1* | 10/2007 | Gazenko ................ | 435/7.32 |
| 2008/0138881 A1 | 6/2008 | Ushiyama et al. | |

FOREIGN PATENT DOCUMENTS

| | | | |
|---|---|---|---|
| JP | 59-106476 | 6/1984 | |
| JP | 64-45374 | 2/1989 | |
| JP | 2-49705 | 10/1990 | |
| JP | 3-15379 | 1/1991 | |
| JP | 4-30798 | 2/1992 | |
| JP | 4-117299 | 4/1992 | |
| JP | 2005-110638 | 4/2005 | |
| JP | 2005-287452 | 10/2005 | |
| JP | 2009-72136 | 4/2009 | |
| JP | 2010-000027 | * 1/2010 | .............. C12Q 1/00 |

(Continued)

OTHER PUBLICATIONS

Machine translation of JP 2009-072136. Obtained from <http://dossier.ipdl.inpit.go.jp/text_trans.html>. Accessed Dec. 14, 2013.*
"Visible and Ultraviolet Spectroscopy," Michigan State University Department of Chemistry; Obtained from <,https://web.archive.org/web/20100712052846/http://www2.chemistry.msu.edu/faculty/reusch/VirtTxtJml/Spectrpy/UV-Vis/spectrum.htm>, Jul. 10, 2010.*
Machine translation of JP 2010-000027, Obtained from <https://worldwide.espacenet.com>, Accessed Jan. 7, 2019.*
Extended Search Report dated Sep. 12, 2013 issued in EP Application No. 11771820.5.
Karmarkar, et al., "Synthesis of p-Nitrophenyl Substituted Tetrazolium Salts Containing Iodine and Other Groups", J.A.C.S., Jul. 20, 1959, vol. 81, No. 14, pp. 3771-3775.

(Continued)

*Primary Examiner* — Alicia L Otton
(74) *Attorney, Agent, or Firm* — Faegre Drinker Biddle & Reath LLP

(57) ABSTRACT

The object of the present invention is to provide a compound used in a reagent for detecting microorganisms, by which microorganisms can be rapidly and reliably detected without requiring any special instrument, the reagent for detecting microorganisms, and a method for detecting microorganisms. The object can be achieved by a tetrazolium compound represented by general formula (I) below:

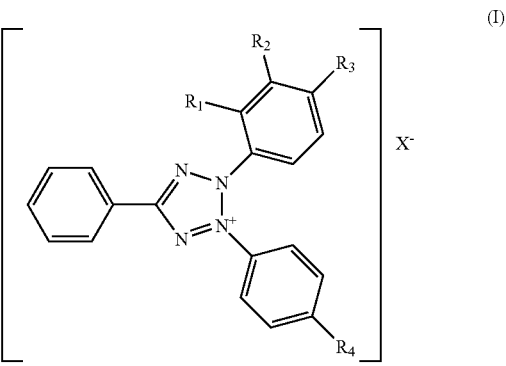

wherein the symbols are as defined in the description, a chromogenic reagent for detecting microorganism comprising the tetrazolium compound, or a method for detecting microorganisms using the chromogenic reagent.

13 Claims, 2 Drawing Sheets

(56) References Cited

FOREIGN PATENT DOCUMENTS

| WO | 97/24432 | 7/1997 |
| WO | 01/44437 | 6/2001 |

OTHER PUBLICATIONS

Kwan-Chung Tsuo, et al., "Synthesis of p-Nitrophenyl Substituted Tetrazolium Salts as Electron Acceptors for the Demonstration of Dehydrogenases", Journal of The American Chemical Society, Dec. 5, 1956, vol. 78, No. 23, pp. 6139-6144.

Aharon Oren, "Then role of glycerol in the nutrition of halophilic archaeal communities: a study of respiratory electron transport", FEMS Microbiology Ecology, Apr. 1, 1995, vol. 16, No. 4, pp. 281-290.

Hans Detlef Klüber, et al., "Characterization of populations of aerobic hydrogen-oxidizing soil bacteria", FEMS Microbiology Ecology, Feb. 1, 1995, vol. 16, No. 2, pp. 167-176.

M.M. Nachlas, et al., "Cytochemical Demonstration of Succinic Dehydrogenase by the Use of a New p-Nitrophenyl Substituted Ditetrazole" Journal of Histochemistry & Cytochemistry, Jul. 1, 1957, vol. 5, No. 4, pp. 420-436.

Mallory, F. B. et al., "Photocyclization of stilbenes and related molecules, Organic Reactions"(Hoboken, NJ, United States), 1984, vol. 30, pp. 309-310.

Vorontsova, L. N., "Synthesis and polarographic reduction of tetrazolium salts", Trudy Instituta Khimii, Ural'skii Nauchnyi Tsentr, Akademiya Nauk SSSR, 1974, vol. 30, 93-9, p. 30, 93-9, Chemical Abstracts, vol. 84, 1976, p. 512, abstract No. 1976:59336.

International Search Report and Written Opinion dated May 17, 2011 in PCT/JP2011/056175 filed Mar. 16, 2011.

Jerchel, et al., "2,3-Diphenylen-tetrazoliumsalse und daraus entstehende Radikale", Just,Lieb. Ann. Der Chemie, Jul. 20, 1954, vol. 590, No. 3, pp. 215-231.

Mallory, F.B., et al., "Photocyclization of Stilbenes and Related Molecules", Organic Reactions, 1984, vol. 30, pp. 1-134, 266-313, and 440-456.

* cited by examiner

[Figure 1]
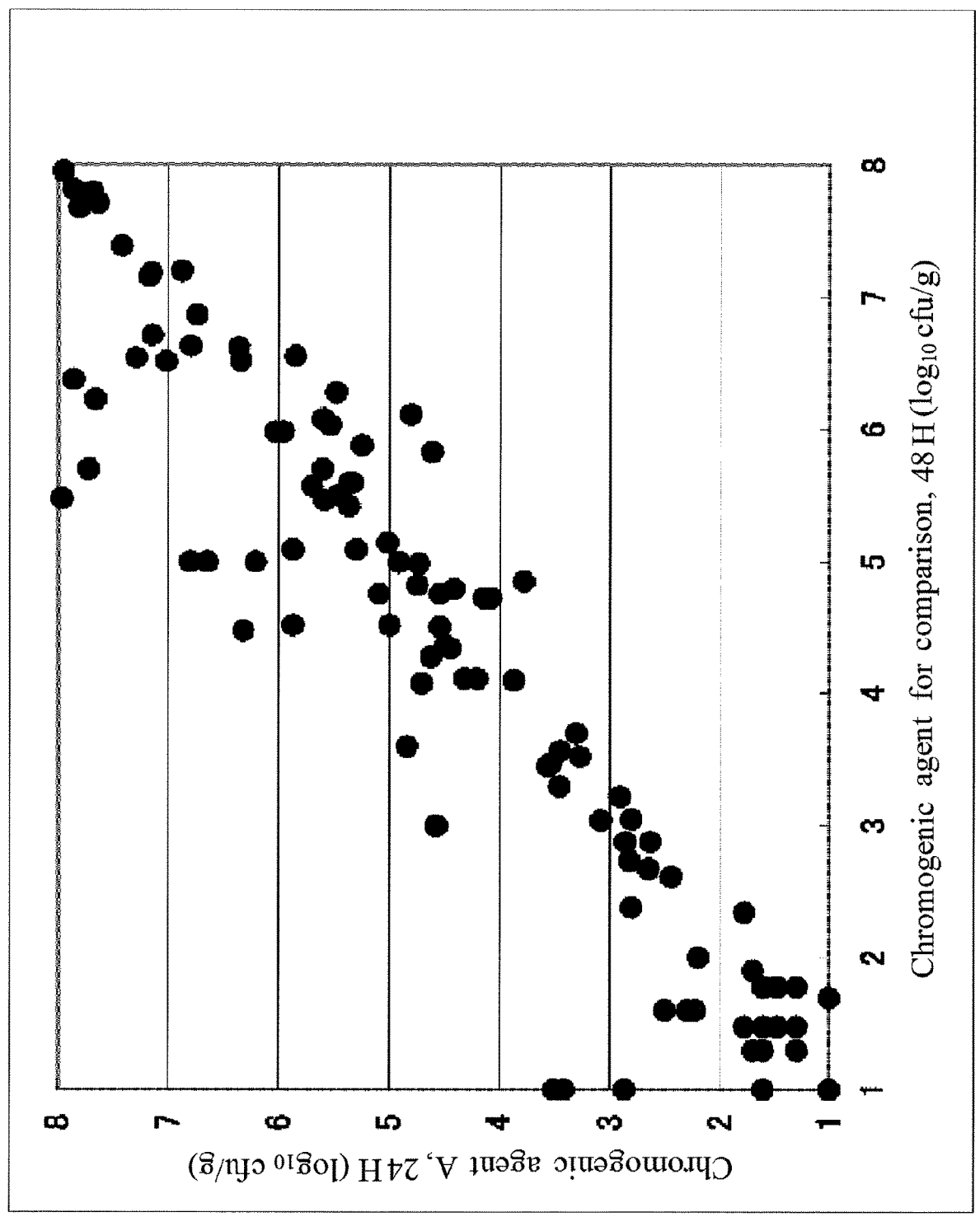

[Figure 2]
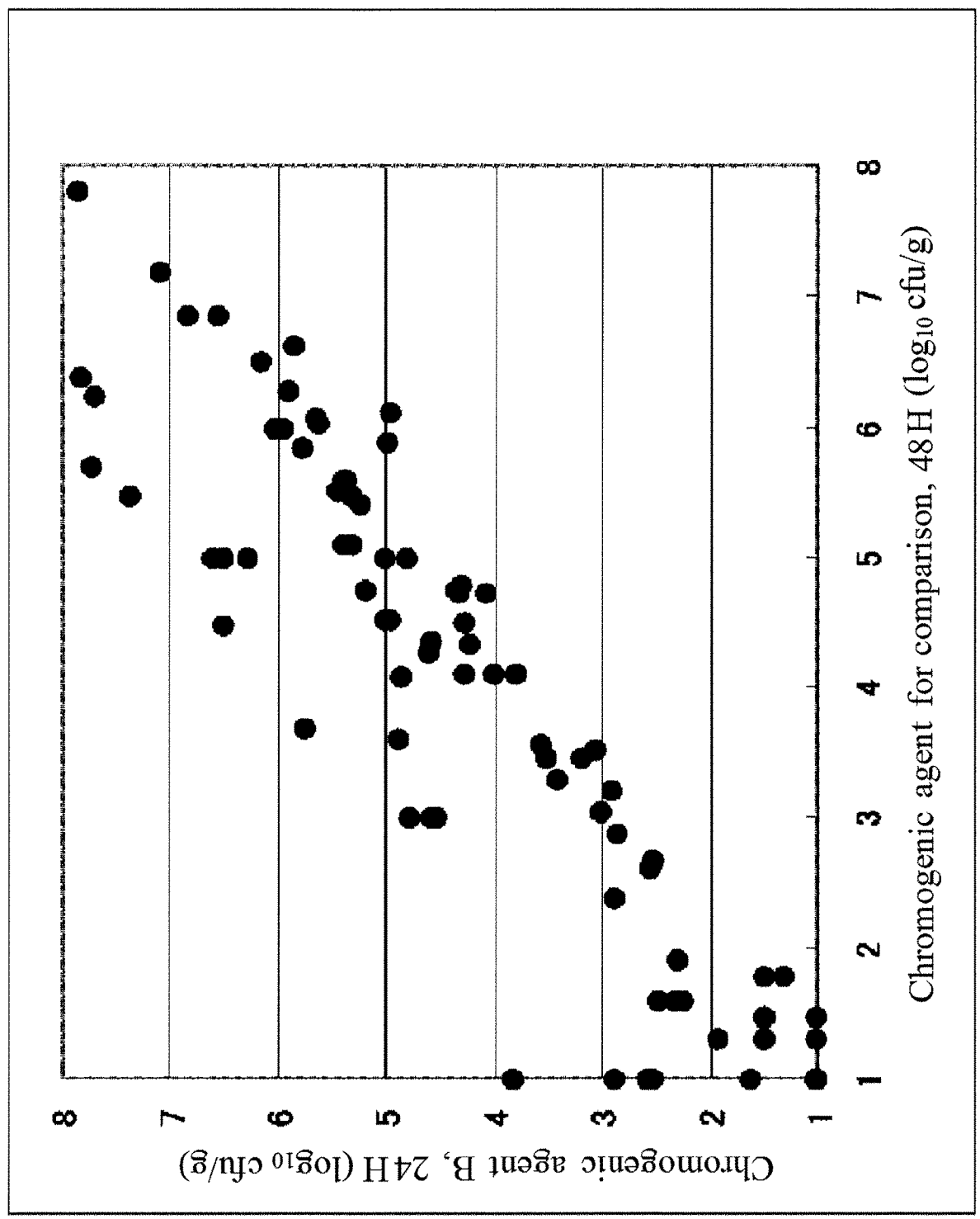

TETRAZOLIUM COMPOUND FOR DETECTING MICROORGANISMS, REAGENT FOR DETECTING MICROORGANISMS AND METHOD FOR DETECTING MICROORGANISMS

CROSS REFERENCE TO RELATED APPLICATIONS

This application is the National Stage of International Application No. PCT/JP2011/056175, filed Mar. 16, 2011, and claims benefit of Japanese Application No. 2010-096510, filed Apr. 19, 2010, all of which are herein incorporated by reference in their entirety.

TECHNICAL FIELD

The present invention relates to a tetrazolium compound, a reagent for detecting microorganisms comprising the compound, and a method for detecting microorganisms.

BACKGROUND ART

Conventional microorganism examination is performed, for example, as follows. First, a powder agar medium is dissolved, sterilized and then kept at a constant temperature. A predetermined amount of the agar medium is dispensed and poured onto a sterile Petri dish previously charged with a predetermined amount of a test sample such as a food suspension or the like. After pouring, the agar is solidified and incubated normally for 24 to 48 hours. The number of the colonies of microorganisms grown is then counted. As such, the conventional method for counting general viable cells involves much time and labor since it requires the preliminary preparation of a culture medium and sterilization of the medium and the agar medium should be maintained at such a temperature as not to solidify the medium, and so on.

Instant culture media of stamp type (cf., e.g., Patent Document 1), filter type or film (sheet) type (cf., e.g., Patent Documents 2 to 4), a type that prevents movement of microorganisms to form colonies on the surface of an incubator device (c.f., e.g., Patent Document 5), test strip type, etc., which are purpose-designed to be easy to use, have also been produced. However, the examination time remains the same as in the case using the agar medium above and it takes 24 to 48 hours or more.

On the other hand, a method as an example that shortens the examination time is involves incubating the collected cells for a short period of time, extracting cell-derived adenosine triphosphate from the cells with a surfactant or an organic solvent, reacting with luciferin in the presence of luciferase to emit light, and detecting the luminescent point with an image analyzer to determine viable cell counts (cf., e.g., Patent Document 6). However, this method requires a special measuring instrument and is normally applicable only to examination of solid-free liquid samples.

A method, which involves contacting a cultured microorganism or a biological sample with a chromogen and confirming the presence of microorganisms by color formation of the chromogen or a fluorescence signal, is disclosed as a method requiring no special measuring instrument (cf., e.g., Patent Documents 7-9). If such a method is used to determine, e.g., the microorganisms in food, the elements in biological samples including sera, whole blood, etc., it might be difficult to detect the microorganisms or elements of interest easily and reliably. This is because an enzymatic reaction necessary for color formation from a chromogen might not proceed smoothly or the colors formed by chromogens might be similar to the colors of food, biological samples, etc., in some occasion.

CITATION LIST

Patent Literature

Patent Document 1: Japanese Unexamined Patent Application Laid-Open No. 4-117299
Patent Document 2: Japanese Examined Patent Publication No. 2-49705
Patent Document 3: Japanese Unexamined Patent Application Laid-Open No. 3-15379
Patent Document 4: WO 2001/44437 Pamphlet
Patent Document 5: WO 1997/24432 Pamphlet
Patent Document 6: Japanese Unexamined Patent Application Laid-Open No. 4-30798
Patent Document 7: Japanese Unexamined Patent Application Laid-Open No. 2005-110638
Patent Document 8: Japanese Unexamined Patent Application Laid-Open No. 2005-287452
Patent Document 9: Japanese Unexamined Patent Application Laid-Open No. 2009-72136

SUMMARY OF INVENTION

Technical Problem

Under the foregoing circumstances, it has been desired to provide a compound which can be used in a microorganism-detecting reagent to detect microorganisms rapidly and reliably without requiring any special instrument, and a reagent for detecting microorganisms as well as a method for detecting microorganisms.

Solution to Problem

The present invention provides a tetrazolium compound, a reagent for detecting microorganisms, the reagent comprising the tetrazolium compound, and a method for detecting microorganisms, as described below.

<1> A tetrazolium compound of formula (I) below:

[Chemical formula 1]

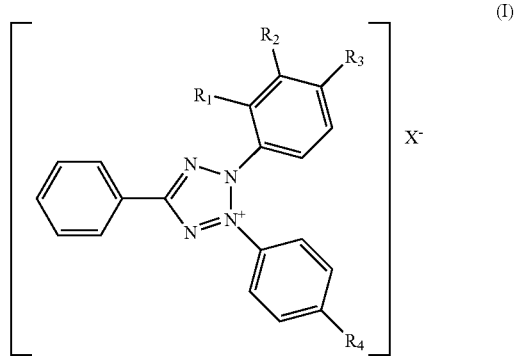

wherein, $R^1$ and $R^2$ each independently is hydrogen or a $C_{1-6}$ alkoxyl (provided that $R^1$ and $R^2$ are not hydrogen at the same time), $R^3$ is hydrogen or nitro, $R^4$ is hydrogen, nitro or a $C_{1-6}$ alkoxyl and $X^-$ is an anion.

<2> The tetrazolium compound according to <1> above, wherein either one of $R^1$ and $R^2$ is a $C_{1-6}$ alkoxyl and another is hydrogen.

<3> The tetrazolium compound according to <2> above, wherein $R^1$ is methoxy, $R^2$ is hydrogen and at least one of $R^3$ and $R^4$ is nitro.

<4> The tetrazolium compound according to <1> above, wherein the tetrazolium compound is a 2-(2-methoxyphenyl)-3-(4-nitrophenyl)-5-phenyltetrazolium salt, 2-(2-methoxy-4-nitrophenyl)-3-(4-nitrophenyl)-5-phenyltetrazolium salt, 2-(2-methoxy-4-nitrophenyl)-3,5-diphenyltetrazolium salt, 2-(2-methoxy-4-nitrophenyl)-3-(4-methoxyphenyl)-5-phenyltetrazolium salt or 2-(3-methoxyphenyl)-3-(4-nitrophenyl)-5-phenyltetrazolium salt.

<5> A chromogenic reagent for detecting microorganisms, the chromogenic reagent comprising the tetrazolium compound according to any one of <1> to <4> above.

<6> The chromogenic reagent for detecting microorganisms according to <5> above, wherein an absorption wavelength region of the formazan dye produced by reduction of the tetrazolium compound is from 400 nm to 420 nm.

<7> A method for detecting microorganisms, which comprises detecting microorganisms by a chromogenic signal of the formazan dye produced from the tetrazolium compound upon contact of a test sample containing microorganisms with the chromogenic reagent according to claim <5> or <6> above.

<8> The method for detection of microorganisms according to <7> above, wherein the chromogenic signal is sensitized by an enzymatic cycling reaction.

Advantageous Effects of Invention

According to the present invention, there are realized the tetrazolium compounds that rapidly generate the reliably detectable chromogenic signals upon contact with microorganisms, etc. By using the tetrazolium compounds, there are also realized the chromogenic reagents and detection method which can detect microorganisms rapidly and reliably without any particular instrument.

BRIEF DESCRIPTION OF DRAWINGS

FIG. 1 is a graph showing the relationship between viable cell counts detected by the chromogenic reagent of Example 1 and viable cell counts detected by the chromogenic reagent of Comparative Example.

FIG. 2 is a graph showing the relationship between viable cell counts detected by the chromogenic reagent of Example 2 and viable cell counts detected by the chromogenic reagent of Comparative Example.

DESCRIPTION OF EMBODIMENTS

1. Tetrazolium Compound

The tetrazolium compound of the present invention has the structure shown by formula (I) above.

1A. Substituents $R^1$ and $R^2$ $R^1$ and $R^2$ each independently is hydrogen or a $C_{1-6}$ alkoxyl but they are not hydrogen at the same time. More specifically, either one of $R^1$ and $R^2$ is a $C_{1-6}$ alkoxyl and another is hydrogen or they are both a $C_{1-6}$ alkoxyl. Preferably, either one of $R^1$ and $R^2$ is a $C_{1-6}$ alkoxyl and another is hydrogen, and more preferably, either one of $R^1$ and $R^2$ is a $C_{1-3}$ alkoxyl. The $C_{1-3}$ alkoxyl is more preferably methoxy. The $C_{1-6}$ ($C_{1-3}$) alkoxyl may have or may not have a substituent such as hydroxy, a halogen, etc. The $C_{1-6}$ ($C_{1-3}$) alkoxyl may or may not be branched.

1B. Substituents $R^3$ and $R^4$ $R^3$ is hydrogen or nitro, and $R^4$ is hydrogen, nitro or a $C_{1-6}$ alkoxyl. Preferably, $R^3$ is hydrogen or nitro, and $R^4$ is hydrogen, nitro or a $C_{1-3}$ alkoxyl. More preferably, $R^3$ and $R^4$ each independently is hydrogen or nitro, and at least one of $R^3$ and $R^4$ is nitro.

1C. Anion $X^-$ is an anion, preferably, a halogen ion such as chloride ion, bromide ion, etc. The anion may also be other anions, e.g., boron tetrafluoride ion.

The tetrazolium compounds described above are easily taken up into the cells of microorganisms, when compared to other tetrazolium compounds, e.g., NBT (nitro blue tetrazolium), etc. For this reason, when the tetrazolium compounds described above are used as the chromogenic reagents for detecting microorganisms, a reduction reaction of the tetrazolium compounds by enzymes rapidly proceeds to form formazan dyes, whereby the microorganisms can be quickly detected. More specifically, it is preferred to use 2-(2-methoxyphenyl)-3-(4-nitrophenyl)-5-phenyltetrazolium chloride (cf., formula (II) below), 2-(2-methoxy-4-nitrophenyl)-3-(4-nitrophenyl)-5-phenyltetrazolium chloride (cf., formula (III) below), 2-(2-methoxy-4-nitrophenyl)-3,5-diphenyltetrazolium chloride (cf, formula (IV) below), 2-(2-methoxy-4-nitrophenyl)-3-(4-methoxyphenyl)-5-phenyltetrazolium chloride (cf., formula (V) below) or 2-(3-methoxyphenyl)-3-(4-nitrophenyl)-5-phenyltetrazolium chloride (cf., formula (VI) below) as the tetrazolium compound of the present invention for detecting microorganisms. Particularly preferred are compounds, in which at least substituent $R^1$ (ortho-position) is methoxy on the 2-phenyl ring, and examples include 2-(2-methoxyphenyl)-3-(4-nitrophenyl)-5-phenyltetrazolium salts (cf., formula (II) below) wherein the substituent $R^3$ (meta-position) is hydrogen on the 2-phenyl ring and the substituent $R^4$ is nitro on the 3-phenyl ring, 2-(2-methoxy-4-nitrophenyl)-3-(4-nitrophenyl)-5-phenyltetrazolium salts (cf., formula (III) below) wherein the 2-phenyl ring further has nitro as the substituent $R^3$, and the like.

[Chemical formula 2]

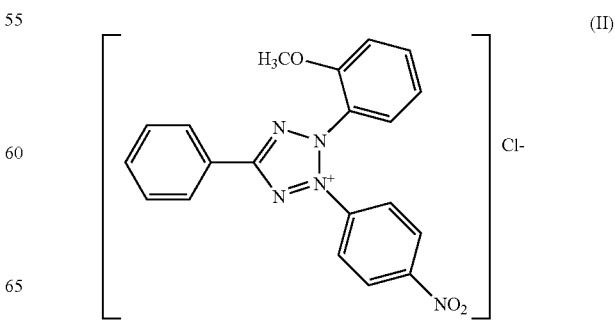

-continued
[Chemical formula 3]
(III)
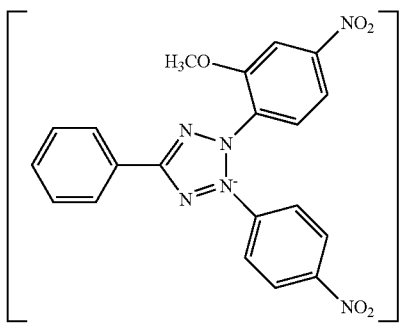
[Chemical formula 4]
(IV)
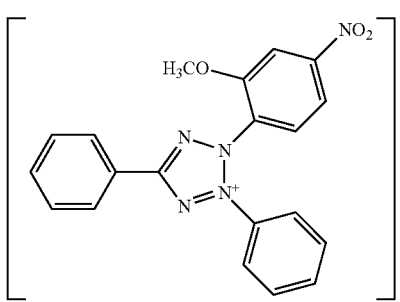
[Chemical formula 5]
(V)
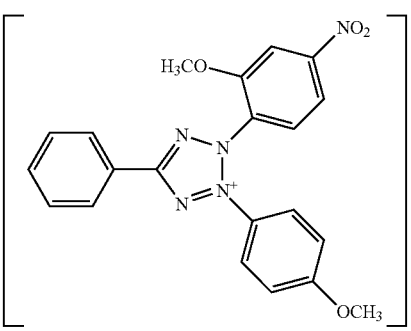
[Chemical formula 6]
(VI)
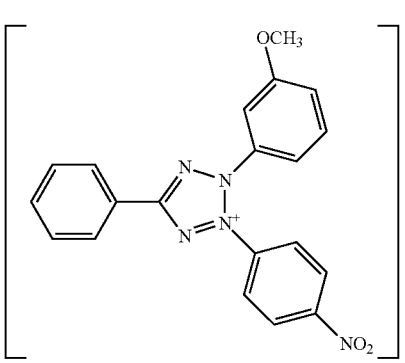
1D. Processes for Synthesis of Tetrazolium Compounds
The tetrazolium compounds of the present invention can be synthesized by any one of the reaction routes described below.
[Chemical formula 7]
(A)
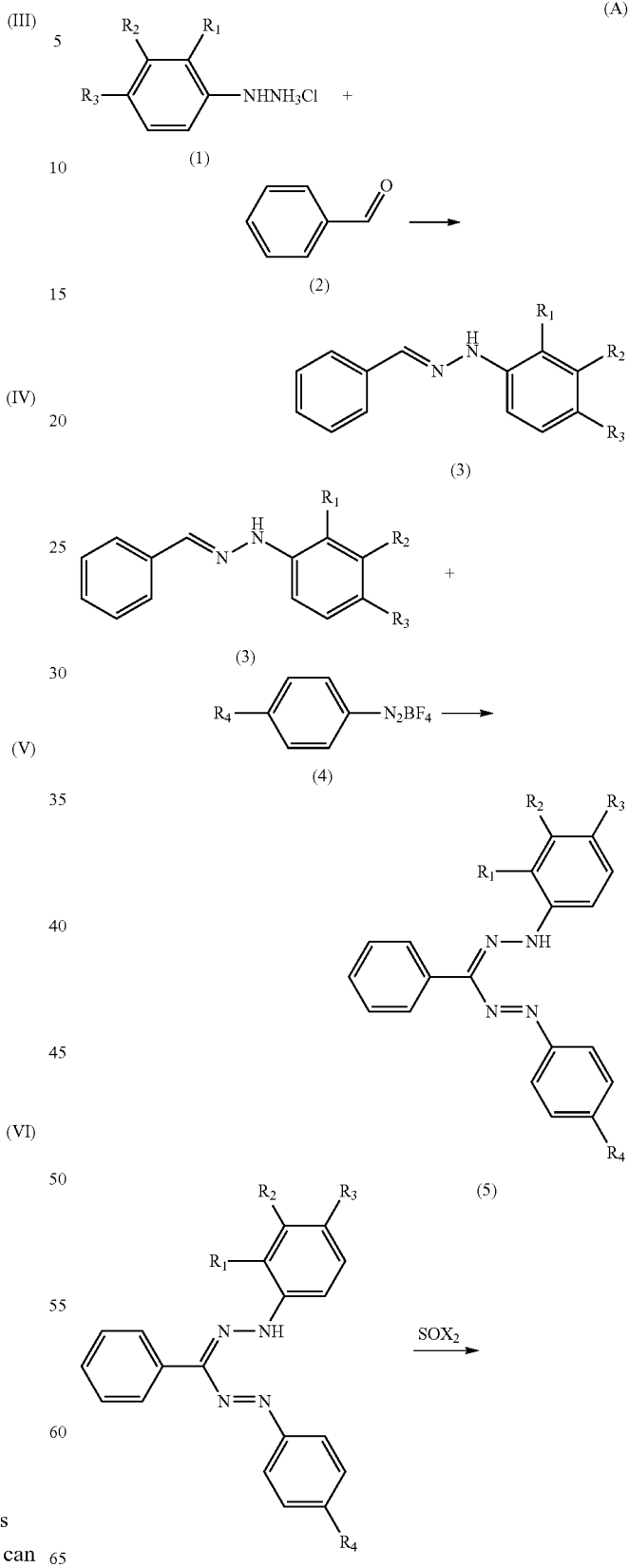

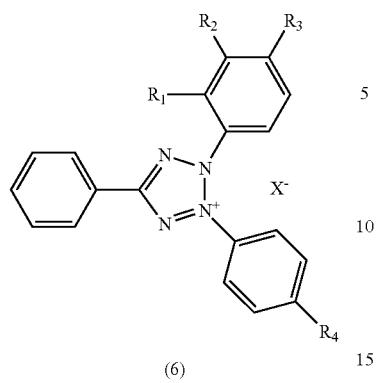

(6)

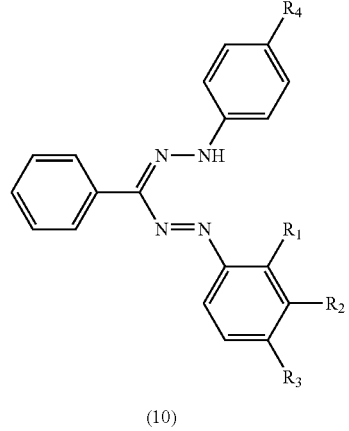

(10)

In the reaction scheme (A), $R^1$ to $R^4$ and $X^-$ are the substituents or ions as defined in formula (I) described above. According to the reaction route shown by the reaction scheme (A), the phenylhydrazine hydrochloride (1) having the substituents $R^1$ to $R^3$ is first reacted with benzaldehyde (2) to form the intermediate (3). This intermediate (3) is reacted with the phenyldiazonium compound (4) having substituent $R^4$ to form the tetrazolium precursor (5). Then, a thionyl halide is reacted with the tetrazolium precursor (5) to give the tetrazolium compound (6) shown by formula (I) above.

[Chemical formula 8]

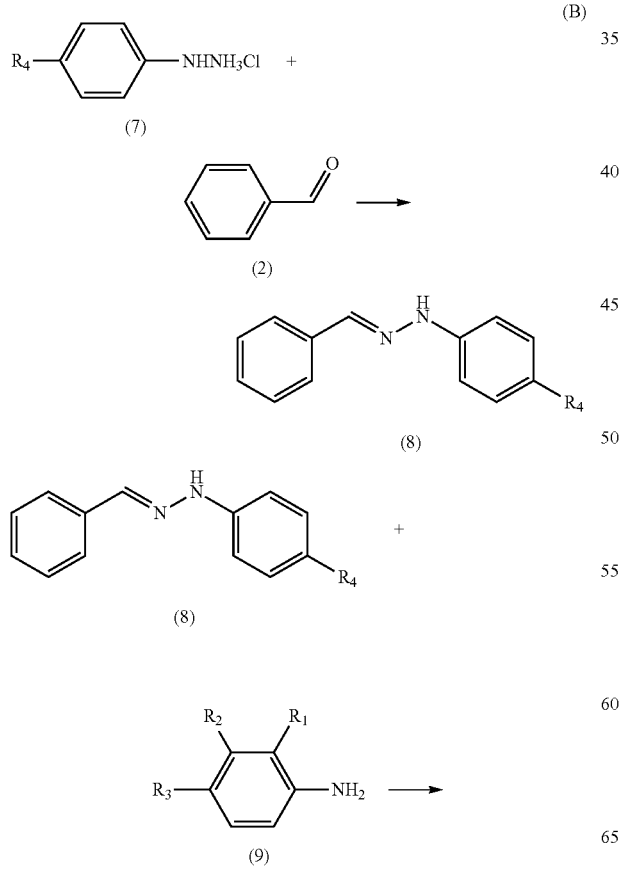

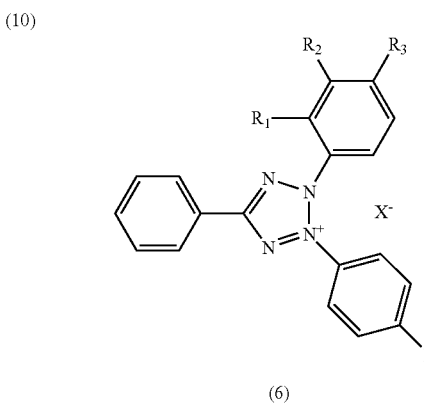

(6)

Also in the reaction scheme (B), $R^1$ to $R^4$ and $X^-$ are the same substituents and ions as defined in formula (I) above. According to the reaction route shown by the reaction scheme (B), the phenylhydrazine hydrochloride (7) having the substituent $R^4$ is first reacted with benzaldehyde (2) to form the intermediate (8). This intermediate (8) is reacted with the aniline derivative (9) having the substituents $R^1$ to $R^3$ to form the tetrazolium precursor (10). Then, a thionyl halide is reacted with the tetrazolium precursor (10) to form the tetrazolium compound (6) shown by formula (I) above. These reaction routes can be appropriately chosen depending upon the structure of target compounds, easy access and availability of materials, etc.

2. Chromogenic Reagent for Detecting Microorganisms

The chromogenic reagent of the present invention for detecting microorganisms comprises one of the tetrazolium compounds described above. Therefore, microorganisms can be rapidly detected. Furthermore, any special measuring instrument is unnecessary in this case and microorganisms can be reliably detected even visually. As such, microorganisms can be reliably detected in a simple manner using the chromogenic reagent of the present invention for detecting microorganisms.

In the chromogenic reagent of the present invention for detecting microorganisms, the formazan dye produced upon reduction of the tetrazolium compound has an absorption wavelength region preferably from 380 nm to 480 nm, more preferably, from 400 nm to 430 nm, and particularly preferably, from 400 nm to 420 nm. In this case, the formazan dye generates blue and bluish purple chromogenic signals. When the tetrazolium compounds for forming chromogenic signals with such cold colors are used as the chromogenic reagents, microorganisms in the target with warm colors such as meat or the like can be detected more reliably by the chromogenic signals with obviously different colors. In general, many warm-colored foods such as meat, etc. are included in the food to be tested for microorganisms, and the above chromogenic reagents for detecting microorganisms enable to detect microorganisms more reliably, when compared with the conventional reagents which form chromogenic signals with warm colors.

3. Method for Detecting Microorganisms

According to the method for detecting microorganisms in the present invention, the chromogenic reagent for detecting microorganisms described above is used. When a sample containing microorganisms is brought in contact with the chromogenic reagent described above, the tetrazolium compound is reduced by an intracellular metabolic reaction of microorganisms to form the formazan dye. Chromogenic signals are formed by this chromogenic formazan.

3A. Enzymatic Cycling Reaction

The chromogenic signal is preferably sensitized by, e.g., an enzymatic cycling reaction. In the enzymatic cycling reaction, there are used the constituents in microorganisms which are relatively highly present, for example, nicotinamide adenine dinucleotide of oxidized type (hereinafter abbreviated as "NAD") and its reduced type (hereinafter abbreviated as "NADH"), or nicotinamide adenine dinucleotide phosphate of oxidized type (hereinafter abbreviated as "NADP") and its reduced type (hereinafter abbreviated as "NADPH"). NAD, NADH, NADP and NADPH are co-enzymes which are highly contained in the living body and participate in an oxidation-reduction reaction of many dehydrogenases through reversible changes via transfer of hydrogen. Accordingly, colors developed by the formazan dye or fluorescence signals derived from the tetrazolium compound, which occur in association with the oxidation or reduction reaction of NAD, NADH, NADP or NADPH, are sensitized by the enzymatic cycling reaction, whereby the presence of NAD, NADH, NADP or NADPH can be detected with high sensitivity. In this case, it is necessary to add dehydrogenase, substrate for the dehydrogenase and diaphorase to the reaction system.

The combination of dehydrogenase and its substrate includes alcohol dehydrogenase [EC1.1.1.1] and methanol, ethanol or propanol, glycerol dehydrogenase [EC1.1.1.6] and glycerin, glycerol 3-phosphate dehydrogenase [EC1.1.1.8] and glycerol 3-phosphate, aldehyde dehydrogenase [EC1.1.1.21] and acetaldehyde, lactate dehydrogenase [EC1.1.1.27] and lactic acid, malate dehydrogenase [EC1.1.1.37] and malic acid, glucose dehydrogenase [EC1.1.1.47] and glucose, glucose 6-phosphate dehydrogenase [EC1.1.1.49] and glucose 6-phosphate, formate dehydrogenase [EC1.2.1.2] and formic acid, aldehyde dehydrogenase [EC1.2.1.3] and acetaldehyde, cholesterol dehydrogenase [EC1.3.1.22] and cholesterol, dehydrogenases of various amino acids shown by Enzyme Commission numbers [EC1.4.1.1 to 20] and various amino acids, etc.

The diaphorase used is derived from *Bacillus stearothermophilus, Clostridium kluyveri* and other microorganisms or derived from swine heart. More preferred are diaphorase I [EC1-6.4.3] and diaphorase II [EC1-6.99.-] derived from *Bacillus stearothermophilus* due to their excellent storage stability. Electron transfer substances such as phenazine methosulfate (PMS), Meldola's blue, etc. may also be used instead of the diaphorase.

3B. Target of Method for Detecting Microorganisms and Range of Its Application

A sample targeted by the method for detecting microorganisms in the present invention is not particularly limited and includes food, cosmetics, experimental equipments, etc. Detectable microorganisms are not particularly limited. The medium may be a liquid medium or a solid medium. Examples of the solid medium are a sheet-form (film-form) medium, a dish-form dry medium, agar medium, a test strip, etc. In relation to the dehydrogenases and their substrates, targets to be tested and media, reference can be made to Japanese Unexamined Patent Application Laid-Open Nos. 2005-110638 and 2005-287452, etc.

The period of time for incubation of microorganisms is sufficient to such a degree that can be observed visually through formation of colored colonies by addition of the chromogenic reagents containing the tetrazolium compounds. In this case, "visual observation" also includes observation through a magnifying glass. The period of time is preferably within 48 hours, and more preferably, within 24 hours. The temperature for incubation can be appropriately determined depending upon the microorganism to be detected.

Next, the present invention will be described with reference to Examples but is not deemed to be limited to these Examples.

Synthesis of Tetrazolium Compounds

Example 1) 2-(2-Methoxyphenyl)-3-(4-nitrophenyl)-5-phenyltetrazolium chloride 2-(2-Methoxyphenyl)-3-(4-nitrophenyl)-5-phenyltetrazolium chloride (hereinafter, tetrazolium compound A, cf., formula (II) described above) was synthesized as follows (cf., formula (VII) below). First, 8 g of 2-methoxyphenylhydrazine hydrochloride was dissolved in 150 ml of water. While stirring at room temperature, a solution obtained by mixing 6 g of benzaldehyde with 75 ml of ethanol was dropwise added to the solution. The mixture was stirred at room temperature for an hour. The precipitates formed were washed with 200 ml of water, dried at 50° C. under reduced pressure to give 10 g of pale yellow solid. This pale yellow solid was dissolved in 600 ml of pyridine and stirred under ice cooling. Subsequently, 12 g of 4-nitrobenzenediazonium tetrafluoroborate was dissolved in 500 ml of water. The solution was dropwise added to the pyridine solution, followed by stirring for 2 hours in an ice bath. The precipitates formed were taken by filtration, washed with 200 ml of water, and dried at 50° C. under reduced pressure to give 8.63 g of blue black solid. The solid was dissolved in 250 ml of toluene and 2 g of thionyl chloride was added thereto, followed by heating at 90° C. for 2 hours with stirring. After cooling, 250 ml of water was added to extract the water-soluble matters. After 250 ml of ethyl acetate was added to the aqueous layer and washed, the aqueous layer was freeze dried to give 5.4 g of 2-(2-methoxyphenyl)-3-(4-nitrophenyl)-5-phenyltetrazolium chloride as yellow solid.

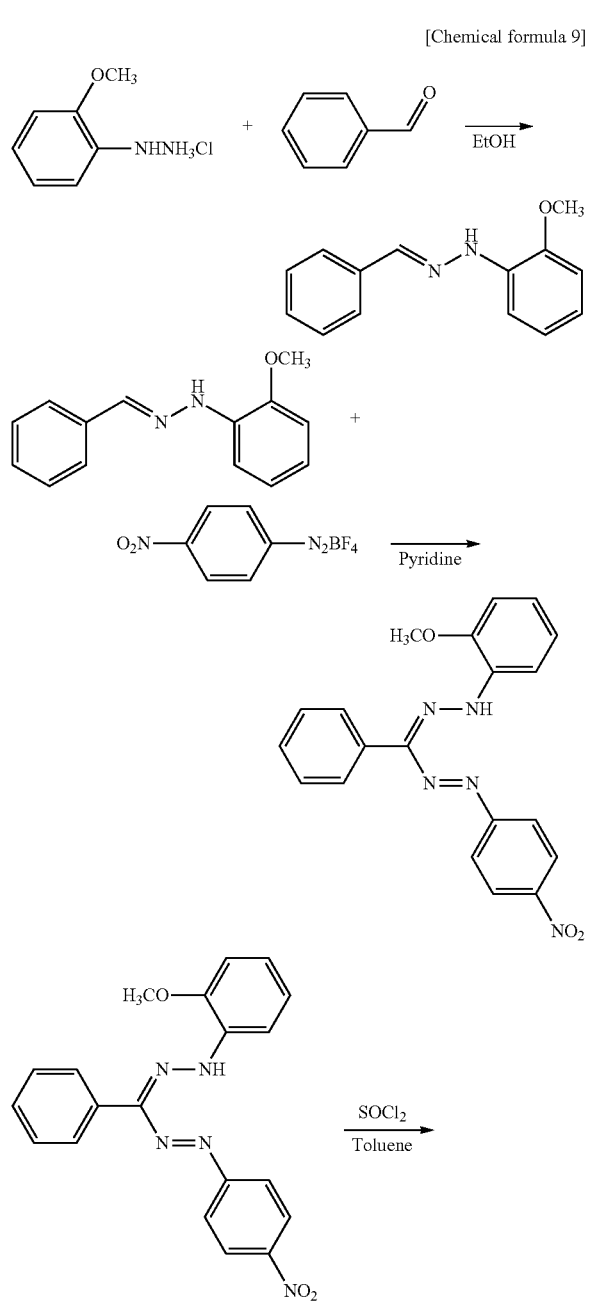

Example 2) 2-(2-Methoxy-4-nitrophenyl)-3-(4-nitrophenyl)-5-phenyltetrazolium chloride 2-(2-Methoxy4-nitrophenyl)-3-(4-nitrophenyl)-5-phenyltetrazolium chloride (hereinafter, tetrazolium compound B, cf., formula (III) above) was synthesized as follows (cf., formula (VIII) below). First, 3 g of 4-nitrophenylhydrazine was dissolved in a mixed solution of 10 ml of conc. hydrochloric acid and 50 ml of water. While stirring at room temperature, a solution obtained by mixing 2.5 g of phenylaldehyde in 20 ml of ethanol was dropwise added to the solution. The resulting mixture was stirred for an hour. The precipitates formed were washed with 200 ml of water and dried at 50° C. under reduced pressure to give 5 g of pale yellow solid. The solid was dissolved in 50 ml of pyridine, and stirred under ice cooling. Next, 5 g of 2-amino-5-nitroanisole was added to a mixed solution of 20 ml of conc. hydrochloric acid and 40 ml of water and stirred under ice cooling. An aqueous solution of 7 g of sodium nitrite in 20 ml of water was dropwise added to the mixture, followed by stirring for an hour in an ice bath. The aqueous solution was dropwise added to the pyridine solution above, and stirred in an ice bath for an hour. The precipitates formed were separated by filtration, washed with 200 ml of water and dried at 50° C. under reduced pressure to give 4.76 g of reddish brown solid. This reddish brown solid was dissolved in 150 ml of toluene, and 2 g of thionyl chloride was added to the solution. The mixture was heated at 90° C. for 2 hours while stirring. After cooling, 150 ml of water was added to extract the water-soluble matters. After 150 ml of ethyl acetate was added to the aqueous layer and washed, the aqueous layer was freeze dried to give 2.54 g of 2-(2-methoxy-4-nitrophenyl)-3-(4-nitrophenyl)-5-phenyltetrazolium chloride as yellow solid.

[Chemical formula 10]

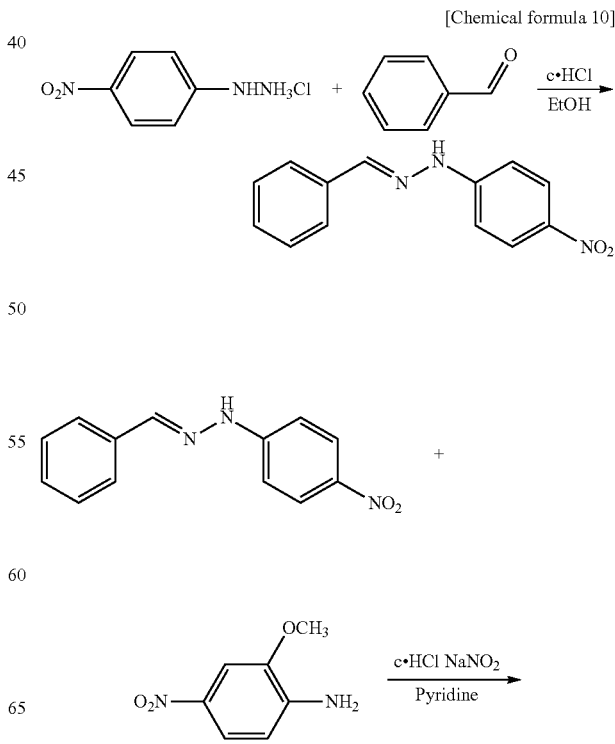

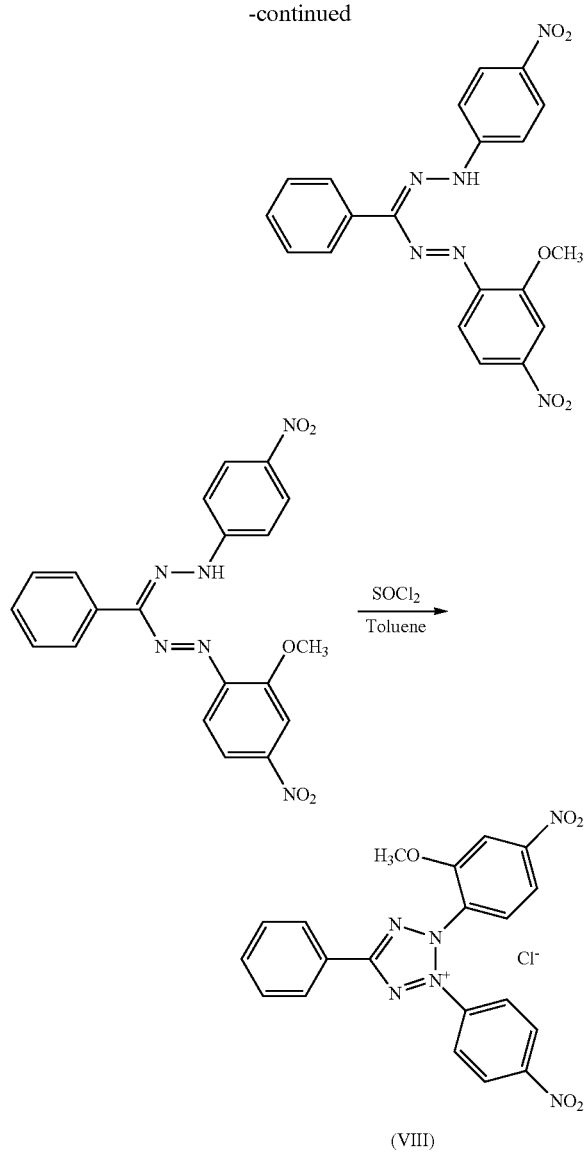

(VIII)

By applying the synthesis process of formula (VII) or (VIII) described above, the aforesaid tetrazolium compounds other than tetrazolium compounds A and B can also be synthesized.

Next, the results obtained by a comparative test for detecting microorganisms using the chromogenic reagent of Example 1 and the chromogenic reagent of Comparative Example are described below. The comparative test was performed as follows. First, sheet media for detecting general viable cells containing as the chromogenic reagent 0.03 g/m³ each of tetrazolium compound A of Example 1 and 2,3,5-triphenyltetrazolium chloride of Comparative Example, respectively, were prepared. The sheet media for general viable cells were the same except that the chromogenic reagents were different.

Then, 10 g of either one of meat, precut vegetables, delicatessens, etc. was put into a sterilized bag and 100 ml of sterile saline was added thereto. The mixture was homogenized with a stomacher. A 10-fold dilution water was prepared using sterile saline, polypropylene films of the two sheets for detecting general viable cells described above were opened to reach the site adhered with a bag sealing tape, and 1 ml each of the dilution above was charged therein. Then, a polypropylene film was placed again to prepare sheet media for detecting general viable cells. Two sheet media for detecting general viable cells, respectively, in Example 1 and Comparative Example were prepared on each of various kinds of food.

The sheet medium of Example 1 for detecting general viable cells containing the chromogenic reagent was incubated for 24 hours and the sheet medium for detecting general viable cells containing the chromogenic reagent for comparison was incubated for 48 hours, respectively, both at 35° C. The viable cell counts were compared between the count of viable cells visually detected by the chromogenic reagent of Example 1 and the count of viable cells detected by the chromogenic reagent of Comparative Example. The results are shown in FIG. 1. Each point in FIG. 1 indicates a logarithmic ratio of the number of colonies in the same food.

As is clear from FIG. 1, the chromogenic reagent by tetrazolium compound A of Example 1 is superior to the chromogenic reagent by the compound of Comparative Example which does not contains the substituents of tetrazolium compound A. In Example 1, notwithstanding that the microorganisms incubated under the same conditions as in Comparative Example except that the incubation time was one-half were detected, almost the same number or more of colonies were detected. As such, it was confirmed that tetrazolium compound A is suitable for use as the chromogenic reagent for detecting microorganisms.

It is considered that these results were achieved because the enzymatic reaction for forming the formazan dye from tetrazolium compound A proceeded rapidly. For this reason, the incubation time was set longer in Comparative Example than in Example 1 to obtain clear results. However, when the chromogenic reagent of Example 1 is actually used, the incubation is sufficient for a shorter period of time, e.g., approximately 16 to 24 hours.

Next, a comparative test was performed in a similar manner using tetrazolium compound B as the chromogenic reagent of Example 2. The compound of Comparative Example is 2,3,5-triphenyltetrazolium chloride, which is the same as in Example 1. The results are shown in FIG. 2. As is clear from FIG. 2, tetrazolium compound B exhibits the same results as in tetrazolium compound A of Example 1. More specifically, notwithstanding that the incubation time is one-half that of Comparative Example, the colonies were detected in the same number as in or more than in Example 2. For this reason it was confirmed that tetrazolium compound B is also superior as the chromogenic reagent for detecting microorganisms to the compound of Comparative Example.

Furthermore, the tetrazolium compounds (cf., formula I above) of the present invention, which have similar molecular structures to tetrazolium compounds A and B, are taken up in the cells of microorganisms more easily than tetrazolium compounds such as NBT, etc., which have larger and more complicated molecular structures. For this reason, the reduction reaction of the tetrazolium compounds by enzymes is considered to proceed rapidly.

The chromogenic reagents by the tetrazolium compounds of the present invention including tetrazolium compounds A and B (cf., formulae (II) and (III) above), which contain methoxy at the ortho-position on the 2-phenyl ring, are more excellent than chromogenic reagents by other tetrazolium compounds, for example, a compound having methoxy only at the para-position on the 2-phenyl ring (substituent $R^3$ in formula (I) above), or a compound having no methoxy (hereinafter the reference compound). This is because the formazan dye produced from the reference compound exhibits a red color, whereas the colors developed by the formazan dye produced from tetrazolium compounds A and B, etc. are blue to bluish purple colors. According to the micro-detection method with the chromogenic reagent of the present invention which forms such a formazan dye, the colonies of microorganisms in samples with warm colors such as meat, etc. can be detected more clearly. Specifically, the peak of absorption wavelength of the formazan dye formed from the reference compound is approximately 430 nm, whereas the peak of absorption wavelength of the formazan dye formed from tetrazolium compounds A and B is approximately 410 nm. As such, the tetrazolium compound of the present invention, which produces the formazan dye having an absorption wavelength region from 400 to 430 nm, and preferably from 400 to 420 nm, is suitable particularly as the reagent for detecting microorganisms.

INDUSTRIAL APPLICABILITY

As described above, the present invention provides the compounds used as the reagents for detecting microorganisms to detect microorganisms rapidly and reliably without requiring any special instrument, the reagents for detecting microorganisms and the method for detecting microorganisms. According to the present invention, microbial contamination in, e.g., food, cosmetics and environments can be detected rapidly and reliably.

The invention claimed is:

1. A sheet- or film-form solid medium for detecting microorganism, wherein the sheet- or film-form solid medium contains a single chromogenic reagent, wherein the single chromogenic reagent is a tetrazolium compound or tetrazolium compounds represented by formula (I):

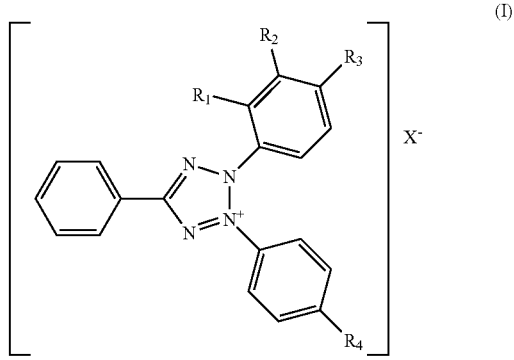

wherein $R^1$ is methoxy, $R^2$ is hydrogen or a $C_{1-6}$ alkoxyl, $R^3$ is hydrogen or nitro, $R^4$ is hydrogen, nitro or a $C_{1-6}$ alkoxyl and $X^-$ is an anion, at least one of $R^3$ and $R^4$ is nitro;
wherein an absorption wavelength region of a formazan dye which is produced by reduction of the tetrazolium compound of formula (I) is from 400 nm to 420 nm;
wherein the formazan dye which is produced by reduction of the tetrazolium compound of formula (I) generates blue or bluish purple chromogenic signals,
wherein the peak of absorption wavelength of the formazan dye formed from the tetrazolium compounds is in the range of 400 nm to 420 nm, and
wherein the sheet- or film-form solid medium is configured so that the tetrazolium compound is taken up by cells of the microorganisms to generate the blue or bluish purple chromogenic signals in contact with the microorganisms to be detected.

2. The sheet- or film-form solid medium according to claim 1, wherein $R^2$ is a $C_{1-6}$ alkoxyl.

3. The sheet- or film-form solid medium according to claim 1, wherein $R^2$ is hydrogen.

4. The sheet- or film-form solid medium according to claim 1, wherein the tetrazolium compound is a 2-(2-methoxyphenyl)-3-(4-nitrophenyl)-5-phenyltetrazolium salt, 2-(2-methoxy-4-nitrophenyl)-3-(4-nitrophenyl)-5-phenyltetrazolium salt, 2-(2-methoxy-4-nitrophenyl)-3,5-diphenyltetrazolium salt, or 2-(2-methoxy-4-nitrophenyl)-3-(4-methoxyphenyl)-5-phenyltetrazolium salt.

5. A method for detecting microorganisms, which comprises contacting a test sample containing microorganisms with the sheet- or film-form solid medium according to claim 1 so that the tetrazolium compound is taken up by cells of the microorganisms, and detecting the microorganism by a blue or bluish purple chromogenic signal produced from the tetrazolium compound.

6. The method for detecting microorganisms according to claim 5, wherein the chromogenic signal is sensitized by an enzymatic cycling reaction.

7. A method for detecting microorganisms, which comprises contacting a test sample containing microorganisms with the sheet- or film-form solid medium according to claim 2 and detecting the microorganism by a blue or bluish purple chromogenic signal produced from the tetrazolium compound.

8. A method for detecting microorganisms, which comprises contacting a test sample containing microorganisms with the sheet- or film-form solid medium according to claim 3 and detecting the microorganism by a blue or bluish purple chromogenic signal produced from the tetrazolium compound.

9. A method for detecting microorganisms, which comprises contacting a test sample containing microorganisms with the sheet- or film-form solid medium according to claim 4 and detecting the microorganism by a blue or bluish purple chromogenic signal produced from the tetrazolium compound.

10. The method for detecting microorganisms according to claim 7, wherein the chromogenic signal is sensitized by an enzymatic cycling reaction.

11. The method for detecting microorganisms according to claim 8, wherein the chromogenic signal is sensitized by an enzymatic cycling reaction.

12. The method for detecting microorganisms according to claim 9, wherein the chromogenic signal is sensitized by an enzymatic cycling reaction.

13. The sheet- or film-form solid medium according to claim 1, wherein the single chromogenic reagent is a tetrazolium compound represented by formula (I).

* * * * *